(12) United States Patent
Warriner et al.

(10) Patent No.: US 9,956,604 B1
(45) Date of Patent: May 1, 2018

(54) RADICAL COMPRESSION APPARATUS AND METHOD OF INCREMENTALLY COMPRESSING AN ARTICLE USING SAME

(71) Applicant: Blockwise Engineering LLC, Tempe, AZ (US)

(72) Inventors: Jeremiah J Warriner, Tempe, AZ (US); Ed Goff, Phoenix, AZ (US)

(73) Assignee: Blockwise Engineering LLC, Tempe, AZ (US)

(*) Notice: Subject to any disclaimer, the term of this patent is extended or adjusted under 35 U.S.C. 154(b) by 0 days. days.

(21) Appl. No.: 15/654,976

(22) Filed: Jul. 20, 2017

Related U.S. Application Data

(63) Continuation of application No. PCT/US2017/017070, filed on Feb. 8, 2017.

(51) Int. Cl.
*B21J 7/16* (2006.01)
*B21J 9/06* (2006.01)
*B21J 9/18* (2006.01)
*B21D 41/04* (2006.01)
*A61F 2/958* (2013.01)
*A61F 2/95* (2013.01)

(52) U.S. Cl.
CPC .............. *B21J 7/16* (2013.01); *B21D 41/045* (2013.01); *B21J 9/06* (2013.01); *B21J 9/18* (2013.01); *A61F 2/958* (2013.01); *A61F 2002/9522* (2013.01)

(58) Field of Classification Search
CPC ......... B21J 7/14; B21J 7/16; B21J 7/46; B21J 9/06; B21D 41/04; B21D 41/045; A61F 2/95; A61F 2002/9522
See application file for complete search history.

(56) References Cited

U.S. PATENT DOCUMENTS

| | | | |
|---|---|---|---|
| 2,458,587 A | 1/1949 | Gogan | |
| 2,999,405 A | 9/1961 | Ewart | |
| 3,695,087 A | 10/1972 | Tuberman | |
| 4,454,657 A | 6/1984 | Yasumi | |
| 5,344,055 A | 9/1994 | Edwards | |
| 6,344,055 B1 | 2/2002 | Shukov | |
| 6,769,161 B2 * | 8/2004 | Brown | A61F 2/958 29/234 |

(Continued)

*Primary Examiner* — Edward Tolan
(74) *Attorney, Agent, or Firm* — Invention To Patent Services; Alex Hobson

(57) ABSTRACT

A radial compression mechanism incorporates an introduction funnel that truncates down to a cylindrical cavity for radial compressing articles. The introduction funnel facilities the loading of an article into the cylindrical cavity and enables incremental radial compression of articles, such as stents. The radial compression mechanism employs a plurality of compression dies that are configured radially about the cylindrical cavity and move in unison to cause the cylindrical cavity to open or close. The compression dies are coupled with a base and drive mechanism for moving them in unison. A method of loading a delivery catheter with a radially compressed article, such as a stent, includes positioning a delivery catheter over a compressed portion of an article that extends from an exit end of the cylindrical catheter. One or more drive mechanism may be used to automatically and incrementally load a compressed article into a delivery catheter.

22 Claims, 15 Drawing Sheets

(56) References Cited

U.S. PATENT DOCUMENTS

| | | | |
|---|---|---|---|
| 6,968,607 B2 | 11/2005 | Motsenbocker | |
| 7,010,953 B2 * | 3/2006 | Stupecky | B21D 39/04 |
| | | | 29/283.5 |
| 7,096,554 B2 * | 8/2006 | Austin | A61F 2/95 |
| | | | 29/282 |
| 7,207,204 B2 * | 4/2007 | Weber | A61F 2/958 |
| | | | 29/234 |
| 7,316,147 B2 * | 1/2008 | Perreault | A61F 2/95 |
| | | | 29/283.5 |
| 7,886,566 B1 | 2/2011 | Knight | |
| 7,886,661 B1 | 2/2011 | Goff et al. | |
| 7,963,142 B2 * | 6/2011 | Goff | A61F 2/95 |
| | | | 29/282 |
| 8,151,445 B1 | 4/2012 | Warriner et al. | |
| 8,245,559 B1 * | 8/2012 | Warriner | B21J 9/06 |
| | | | 29/516 |
| 8,468,667 B2 | 6/2013 | Straubinger et al. | |
| 2004/0096538 A1 | 5/2004 | Goff et al. | |
| 2005/0154450 A1 | 7/2005 | Larson et al. | |
| 2005/0251194 A1 | 11/2005 | McHale | |
| 2008/0127707 A1 | 6/2008 | Kosish et al. | |
| 2009/0049675 A1 | 2/2009 | Sokel et al. | |
| 2011/0162432 A1 | 7/2011 | Perreault et al. | |
| 2011/0239428 A1 | 10/2011 | Motsenbocker | |

\* cited by examiner

RADICAL COMPRESSION APPARATUS AND METHOD OF INCREMENTALLY COMPRESSING AN ARTICLE USING SAME

CROSS REFERENCE TO RELATED APPLICATIONS

This application claims the benefit of international application no. PCT/US17/17070, filed on Feb. 8, 2017, which claims the benefit of U.S. provisional patent application No. 62/292,851, filed on Feb. 8, 2016, the entirety of both applications are hereby incorporated by reference herein.

BACKGROUND OF THE INVENTION

Field of the Invention

This invention relates to radial compression mechanisms and methods of radially compressing articles, particularly stents, catheters, balloons, and the like.

Background

During the manufacturing and packaging process of self-expanding stents, used primarily as percutaneous vascular implants to promote the free flow of blood through diseased arterial restrictions, it is necessary to compress the expanded stent and load the stent into a delivery system. Typically, the stents are compressed using a radial compression mechanism like that disclosed in U.S. Pat. No. 7,886,661 or U.S. Pat. No. 6,968,607 to approximately the inner diameter of the delivery catheter or tube. Then with the opening of delivery catheter aligned with opening of the radial compression mechanism and with the tip of the catheter positioned so that there is little or no gap between the tip of the catheter and the face of the radial compression mechanism, the stent is pushed through the compression mechanism into the catheter with a rod-like device.

There are a number of deficiencies of the current state-of-the-art process. First, the length of the radial compression mechanism must be at least as long as the compressed length of the stent. Self-expanding stent manufacturers are trending towards longer stents and having the length of the stent related to the length of the radial compression mechanism causes a number of problems. To start, long length radial compression mechanisms are much more difficult to manufacture than short length radial compression mechanisms. The tolerances required to produce a sufficiently accurate radial compression mechanism necessitates the use of demanding manufacturing processes. In general, the difficulty to maintain the required tolerances increases with the size of the parts. For example, shorter length compression dies are much easier to manufacture accurately than long dies.

A long radial compression mechanism is also more susceptible to compliance that can reduce the accuracy of the loading system. As an example, the triangular shaped dies of a radial compression mechanism are typically supported on the ends while the loading occurs over the entire length of the die. The longer the die is, the more a given load will move the die from its unloaded position.

A relatively long compression mechanism also requires more force to operate. The force to compress a stent is approximately linearly proportional to its length and therefore a longer radial compression mechanism will require proportionally more force to operate than a shorter one. In addition to compounding the compliance problem noted above, a higher force requirement generally means bigger, more expensive, and less accurate actuators and sensors. It also requires proportionally larger support components, with the accompanying downsides of cost and weight, or sacrificing performance with greater inadvertent deflections or higher stresses.

Another drastic shortcoming of the current state-of-the-art process is the need to use low friction materials for the construction of the radial compression mechanism dies or working surfaces. The friction must be low since the stent must translate through the device in its compressed state. This requirement generally precludes the use of more durable materials such as hardened stainless steel in favor of plastics with low friction properties. Plastics cannot typically be manufactured to the tolerances that metals, like stainless steel, can and when employed as the die material of a radial compression mechanism, the accuracy of the mechanism suffers.

In the traditional stent loading process, the sliding of the stent across the radial compression dies causes wear on the dies. Wear causes a deterioration in performance and ultimately requires that the dies be refinished or replaced. The process of wearing also generates particulate that can potentially contaminate the stent implant.

It would be highly advantageous to remedy the deficiencies in the current stent-loading mechanisms and associated processes.

It is the object of the present invention to provide a radial compression mechanism and process that decouples the length of the stent from the radial compression mechanism. A shorter length radial compression mechanism will generally be more accurate, have lower force requirements, and cost much less to produce.

Another objective of the present invention is to provide a radial compression mechanism and process that does not depend on sliding action between the stent and mechanism and can therefore use durable materials in its construction

SUMMARY OF THE INVENTION

The present invention relates to radial compression mechanisms, such as those described in U.S. Pat. No. 7,886,661, to Goff, et al., U.S. Pat. No. 8,245,559, to Warriner et al., and U.S. Pat. No. 6,968,607 to Motsenbocker; the entirety of which are hereby incorporated by reference herein. These patents describe radial compression mechanisms that comprise a plurality of dies arranged to create an approximately cylindrical opening, used to uniformly compress a stent or other device to a smaller diameter.

An exemplary radial compression mechanism of the present invention comprises a plurality of compression dies having a compression portion and an introduction portion. The compression portions of the compression dies form a centrally located cylindrical cavity for radially compressing stents and other devices. The introduction portions of the compression dies create an introduction funnel that facilitates the insertion of a device to be radially compressed in the cylindrical cavity. In an exemplary embodiment, the die working surfaces of the compression dies form the centrally located cylindrical cavity and the die working surfaces are planar wherein adjacent compression dies have parallel die working surfaces. In an exemplary embodiment, the introduction surfaces of the compression dies form the introduction funnel, wherein the introduction surfaces are planar and wherein adjacent compression dies have parallel introduction surfaces. The plurality of compression dies are arranged radially with respect to each other to form a generally centrally located cylindrical cavity defined by the working surface and having a length from an inlet end and an exit end. The plurality of introduction portions of the dies are also arranged radially with respect to each other to form the introduction funnel defined by the introduction surfaces and having a length from an attached end to the extended end. The introduction portions of at least some of the plurality of compression dies may be integrally attached to the compression portion, wherein the introduction portion and the compression portion are made from a single piece of material such as through machining or casting, for example, to form a one-piece unit.

An exemplary radial compression mechanism comprises a base and a plurality of compression dies that are coupled to said base and configured to move with respect to the base in unison from an open position to a closed position. The plurality of compression dies are arranged radially with respect to each other to form a generally cylindrical cavity defined by the die working surfaces. The cylindrical cavity has a length from an inlet end to an exit end. This length may be any suitable length, including, but not limited to, no more than about 25 cm, no more than 10 cm, no more than 5 cm, no more than 2.5 cm, no more than 1 cm, no more than 0.5 cm and any range between and including the length values provided. The longer the length the greater the forces required for compression which means larger drives may be required for compression. In an exemplary embodiment, a radial compression mechanism and method are described for incrementally radially compressing an article and indexing the article through the radial compression mechanism. In this embodiment, it may be preferred to maintain the length of the cylindrical cavity to no more than 5 cm, no more than 2.5 cm, no more than 1 cm, no more than 0.5 cm and any range between and including the length values provided. These relatively short lengths may reduce the compression force required.

An exemplary cylindrical cavity may be configured to open to a diameter that is at least as large as the length of the cylindrical cavity and may be some factor larger, such as about two or more, about five or more, about ten or more and any range between and including the factors provided. For example, the length of the cylindrical cavity may be about 5 mm and the maximum open diameter of the cylindrical cavity may be 5 mm, or 10 mm or 20 mm. A cylindrical cavity may be configured to accommodate parts of a wide range of sizes and may have a cylindrical cavity diameter, when in an open position, of about 12 mm or more, about 25 mm or more, about 50 mm or more, about 75 mm or more, about 100 mm or more and any range between and including the open position cylindrical cavity diameters provided. A cylindrical cavity may be configured to close to a completely closed orientation, wherein the die working surface touch, or may close to a closed position having a diameter of about 50 µm or less about 100 µm or less, about 150 µm or less and any range between the diameter values provided.

An exemplary introduction portion of a radial compression mechanism is configured with introduction surfaces that are at an introduction angle to the die working surfaces, or a central axis extending through the cylindrical cavity, to from an introduction funnel. The introduction angle is an acute angle and may be no more than about 60 degrees, no more than about 45 degrees, no more than about 30 degrees, no more than about 15 degrees, no more than about 10 degrees, no more than 5 degrees and any range between and including the introduction angles provided. An introduction having a high introduction angle may be too blunt and cause high friction as an article to be compressed is reduced down in diameter quickly to the cylindrical cavity diameter. In addition, the length of the introduction portion may be selected with attention to the introduction angle and the types of articles to be radially compressed to ensure proper function of the radial compression mechanism. The length of the introduction surfaces may be at least the length of the cylindrical cavity or longer. The introduction surfaces may be planar and extend from the die working surface, or attached end, to an extended end, wherein the extended ends form a larger diameter opening than the inlet opening to the cylindrical cavity.

The plurality of dies move to change both the cylindrical cavity diameter and the introduction funnel diameter, wherein the funnel reduces in diameter along the length of the introduction surfaces. An article configured to be radially compressed may be subjected to pre-compression by the introduction funnel as it closes down during the radial compression of a first portion of the article configured in the cylindrical cavity. This pre-compression may facilitate the incremental insertion of the article into the cylindrical cavity and may reduce forces for radial compression.

The die working surfaces and/or the introduction surfaces of adjacent compression dies may touch each other or may be configured with a gap therebetween. In an exemplary embodiment, a gap distance between adjacent dies is maintained throughout the opening and closing of the cylindrical cavity. An exemplary gap distance between die working surfaces and/or introduction surfaces may be no more than 250 µm, and preferably no more than 100 µm, and more preferably no more than 50 µm. In a particularly preferred embodiment, the gap distance is maintained below 25 µm. A small gap provides a substantially continuous contact surface for parts to slide through the radial compression mechanism. A substantially continuous cylindrical cavity surface and/or introduction surface is a surface defined by the plurality of compression dies wherein there is no more than a 50 µm gap between the dies, and preferably no more than 25 µm.

An exemplary radial compression mechanism comprises at least three compression dies that form a cylindrical cavity, and may comprise ten or more, fourteen or more, and the like. In most cases however, a radial compression mechanism, as described herein, will comprise six to fourteen compression dies, thereby forming a more cylindrical shaped cylindrical cavity. The more compression dies utilized, the more circular in cross-section shape the cylindrical cavity becomes. For example, a radial compression mechanism employing eight compression dies will have an octagon shaped cylindrical cavity and a compression mechanism employing ten compression dies will have a decagon shaped cylindrical cavity. On the other hand, the more compression dies employed, the more complicated the assembly becomes.

The plurality of radial compression dies are configured radially about the centrally located cylindrical cavity and are coupled to a base. The plurality of compression dies move relative to the base to open and close the cylindrical cavity. In one embodiment, the plurality of dies rotate or pivot about a point, such as a post or pin. In another embodiment, the plurality of dies slide along a cam surface which may have a straight or curved orientation. In another embodiment, the plurality of compression dies rotate and move in combination to uniformly reduce the diameter of the central cylindrical cavity. Any suitable arrangement to move the compression dies may be used. A drive mechanism may be coupled with the plurality of compression dies to move them and open and close the introduction funnel and the cylindrical cavity. A drive mechanism may be a hand operated lever, a linear motion actuator, a motor, such as a servomotor and the like.

An exemplary radial compression mechanism may be used to compress a stent or other article in an incremental method. A first portion of an article may be inserted through the introduction funnel and into the cylindrical cavity. The compression dies may then be closed to a compressed diameter, a desired diameter of the article. The compression dies may then be opened to a larger diameter than the compression diameter and the article may be indexed through the radial compression mechanism, wherein the portion of the article compressed is pushed out of the exit end of the cylindrical cavity and a new portion of the article is now located within the cylindrical cavity. Again, the compression dies may be closed to a compressed diameter and subsequently re-opened. This process may be repeated until the entire article is radially compressed or at least a desired portion is radially compressed. The cycle for compressing a portion of an article may be rather quick, such as about one cycle per second or more, about five cycles per second or more, about ten cycle per second or more, about 30 cycle per second or more, about 60 cycle per second or more and any range between and including the cycle times provided.

In another exemplary method, a delivery catheter, is positioned at the exit end of the cylindrical cavity and receives the compressed portions of the article therein. A delivery catheter, as used herein, includes any conduit for receiving a compressed article and may be a catheter, a sleeve, tube and the like. A delivery catheter may be pushed over a compressed article that is extending out from the cylindrical cavity while the cylindrical cavity is in a compressed diameter. In this way, the compressed article is retained in position which allows the delivery catheter to be pushed thereover. When the cylindrical cavity opens and a new portion of the article is pushed into the cylindrical cavity, a new compressed portion is pushed out, and extends from the exit end of the cylindrical cavity. Again, when the cylindrical cavity closes, the delivery catheter can be pushed thereover. This process may be repeated until an article is fully inserted into a delivery catheter. These incremental steps may facilitate insertion of a compressed article into a delivery catheter as the relative short compressed portions require less force than attempting to slide an entire length of a compressed article into a delivery catheter. In this exemplary method of incrementally compressing and loading an article into a delivery catheter, two actuators, one for the radial compression mechanism and the other to translate the delivery catheter over the compressed portions of the stent may be employed. Many different types of actuators could be employed for either task, ranging from a manually actuated system, to pneumatic, to electrically actuated systems and the like. As it is advantageous for the loading cycle to be completed as quickly as possible to reduce the loading time of the stent, in one preferred embodiment, the radial compression mechanism uses a directly coupled angular motor and the delivery catheter is attached to a linear electric motor. Both motors may be designed for high frequency use.

Furthermore, since the introduction funnel section of the radial compression mechanism gradually reduces the diameter of the stent until it reaches the cylindrical cavity, a compression mechanism that is much shorter than the length of the stent can be used to load the stent. This mechanism and process decouples the length of the compression station from the length of the stent. This reduction in length results in a more accurate mechanism, has lower actuating forces, and is considerably less costly to manufacture.

In another exemplary embodiment, a cooling system is provided to cool the compressed stent or the delivery catheter to facilitate maintaining the compressed article in a compressed state. A cooling system may cool the compressed article and/or the deliver catheter to freezing temperatures or less, such as cryogenic temperatures and the like. A cooling system may be used to keep a stent from expanding after compression. Most typically, self-expanding stents are fabricated with Nitinol that is heat treated such that at room or body temperature, the stent material exhibits super-elastic properties, or is in an austenitic phase. When the stent is cooled below a certain temperature, the stent no longer exhibits the super-elastic behavior, is in martensitic phase, and will not rebound to its expanded state after compression. This temperature dependency can be exploited as an aid in loading. Loading cold can lower the radial force of the stent applied to the inside of the delivery catheter and consequently the force required to translate the stent inside the delivery catheter.

The summary of the invention is provided as a general introduction to some of the embodiments of the invention, and is not intended to be limiting. Additional example embodiments including variations and alternative configurations of the invention are provided herein.

BRIEF DESCRIPTION OF THE DRAWINGS

The accompanying drawings are included to provide a further understanding of the invention and are incorporated in and constitute a part of this specification, illustrate embodiments of the invention, and together with the description serve to explain the principles of the invention.

DETAILED DESCRIPTION OF THE ILLUSTRATED EMBODIMENTS

Figure 1:
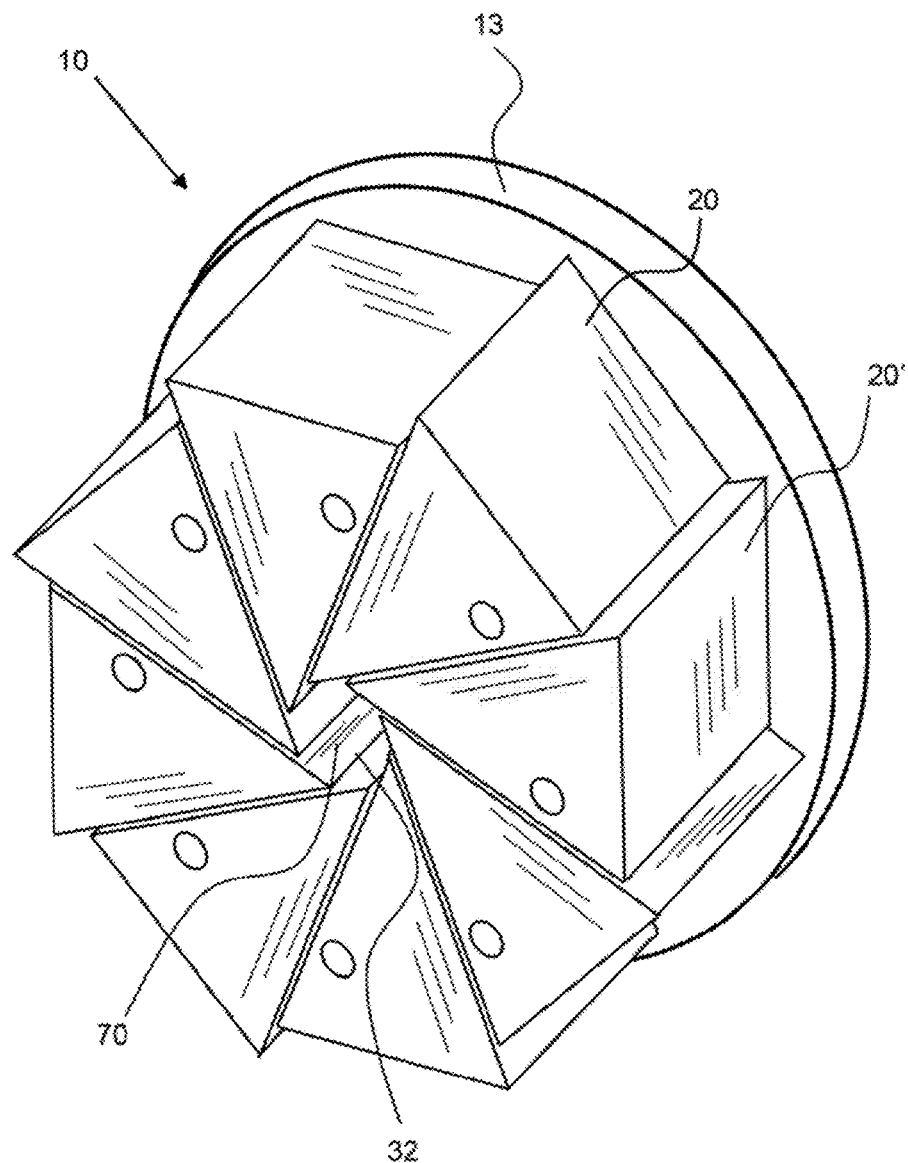
FIG. 1 shows a perspective view of an exemplary radial compression mechanism comprising a plurality of compression dies coupled to a base.

Corresponding reference characters indicate corresponding parts throughout the several views of the figures. The figures represent an illustration of some of the embodiments of the present invention and are not to be construed as limiting the scope of the invention in any manner. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Certain exemplary embodiments of the present invention are described herein and are illustrated in the accompanying figures. The embodiments described are only for purposes of illustrating the present invention and should not be interpreted as limiting the scope of the invention. Other embodiments of the invention, and certain modifications, combinations and improvements of the described embodiments, will occur to those skilled in the art and all such alternate embodiments, combinations, modifications, improvements are within the scope of the present invention.

As shown in FIG. 1, an exemplary radial compression mechanism 10 comprises a plurality of compression dies 20, 20' configured radially about a central cavity 70 and coupled to a base 13. The plurality of compression dies are configured to move with respect to the base to open and close the cylindrical cavity 70. The working surfaces 32 of the compression dies form the expanding and contracting cylindrical cavity. In this embodiment, there are eight compression dies and therefore the central cavity is an octagon.

Figure 2:
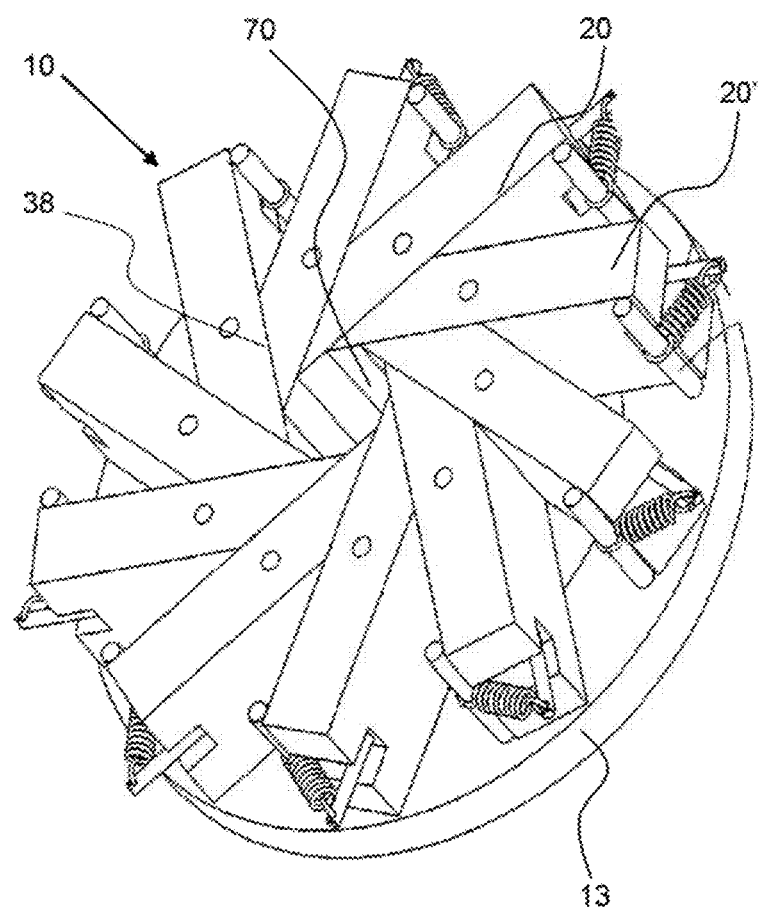
FIG. 2 shows a perspective view of an exemplary radial compression mechanism comprising a plurality of compression dies coupled to a base.

As shown in FIG. 2, an exemplary radial compression mechanism 10 comprises a plurality of compression dies 20, 20' configured radially about the base 13 to form a central cylindrical cavity 70. The compression dies have an interface surface 38, or surface between adjacent compression dies. In some embodiments, the compression dies may be configured to slide along the interface surfaces and in another embodiment a gap may be formed between the interface surfaces. In this embodiment, the radial compression mechanism 10 comprises ten compression dies and therefore the cylindrical cavity is a decagon shape.

Figure 3:
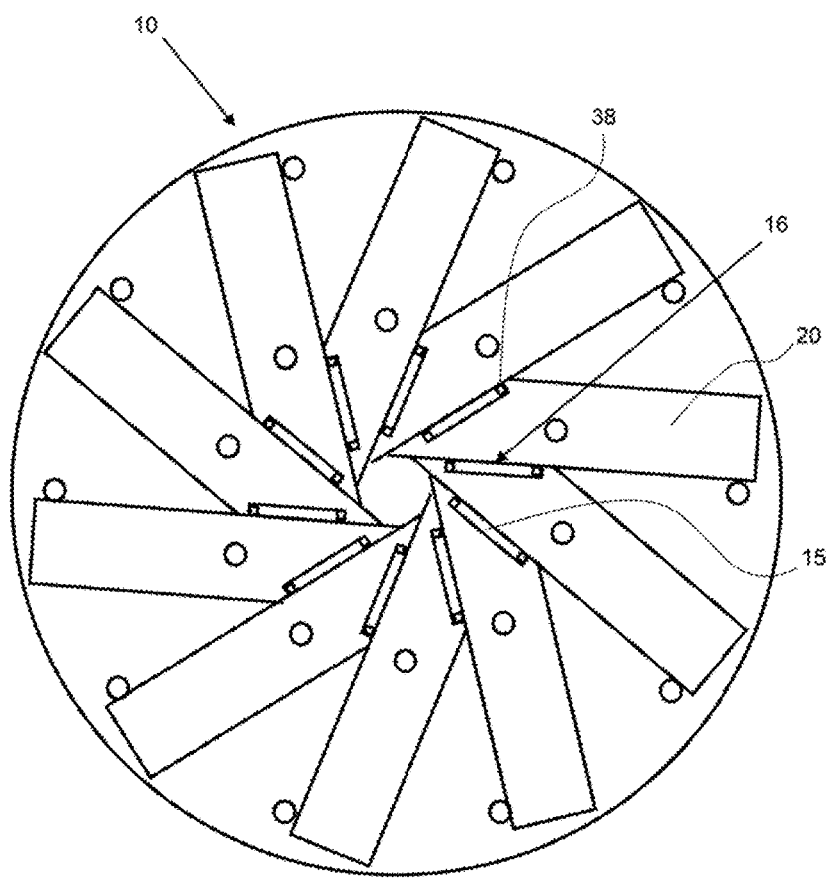
FIG. 3 shows a front view of an exemplary radial compression mechanism comprising bearings between the plurality of compression dies.

As shown in FIG. 3, an exemplary radial compression mechanism 10 comprises bearings 15 between the interface surfaces 38 of the plurality of compression dies 20. Bearings 15 are configured between the interface surfaces 38 to form a gap 16 between adjacent compression dies 20.

Figure 4:
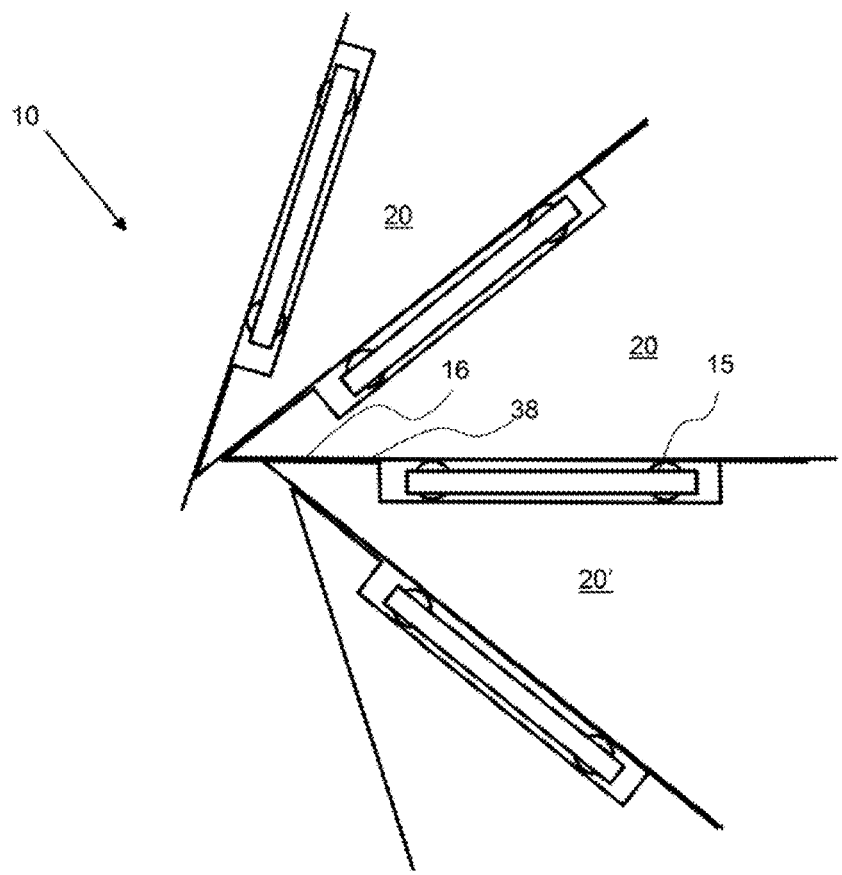
FIG. 4 shows an expanded view of the radial compression mechanism shown in FIG. 3.

FIG. 4 shows an expanded view of the radial compression mechanism shown in FIG. 3. The bearing 15 is configured between the interface surface 38 to form a gap 16 between the two adjacent compression dies 20, 20'.

Figure 5:
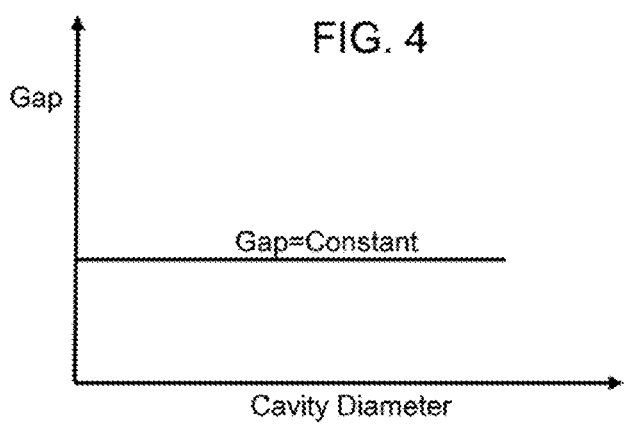
FIG. 5 shows a graph of the gap distance between adjacent compression dies as a function of the cavity diameter.

FIG. 5 shows a graph of the gap distance between adjacent compression dies as a function of the cavity diameter. As shown, the gap distance between the two adjacent dies remains constant as the central cylindrical cavity is opened and closed.

Figure 6:
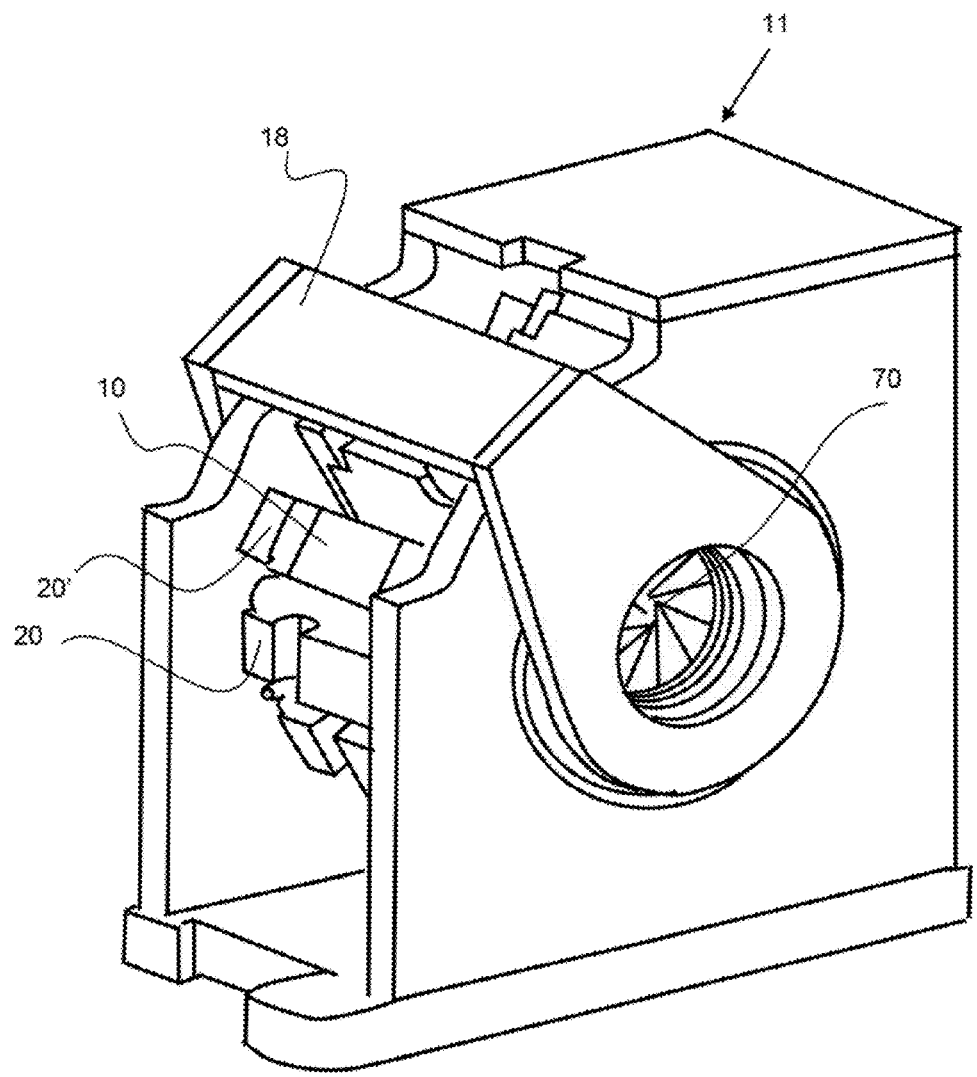
FIG. 6 shows a perspective view of an exemplary radial compression apparatus having a radial compression mechanism coupled to a drive mechanism.

As shown in FIG. 6, an exemplary radial compression apparatus 11 has a radial compression mechanism 10 coupled to a drive mechanism 18. The diameter of the central cylindrical cavity 70 is opened and closed by the movement of the drive mechanism. The drive mechanism rotates a base that is coupled to the compression dies.

Figure 7:
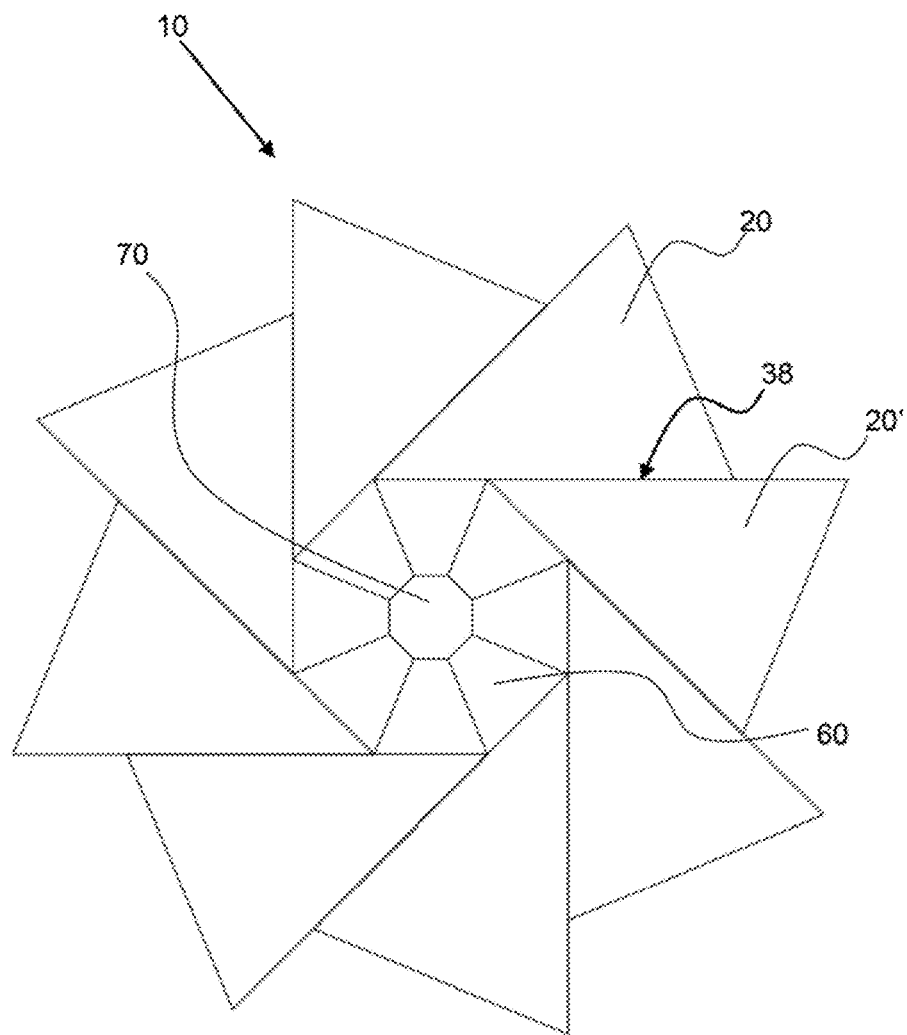
FIG. 7 shows a front view of an exemplary radial compression mechanism comprising a plurality of compression dies configured radially about a central cylindrical cavity and having an introduction funnel.

As shown in FIG. 7, an exemplary radial compression mechanism 10 comprises a plurality of compression dies 20 configured radially about a central cylindrical cavity 70 and has an introduction funnel 60. The compression dies have an interface surface 38 between adjacent compression dies, 20, 20', for example.

Figure 8:
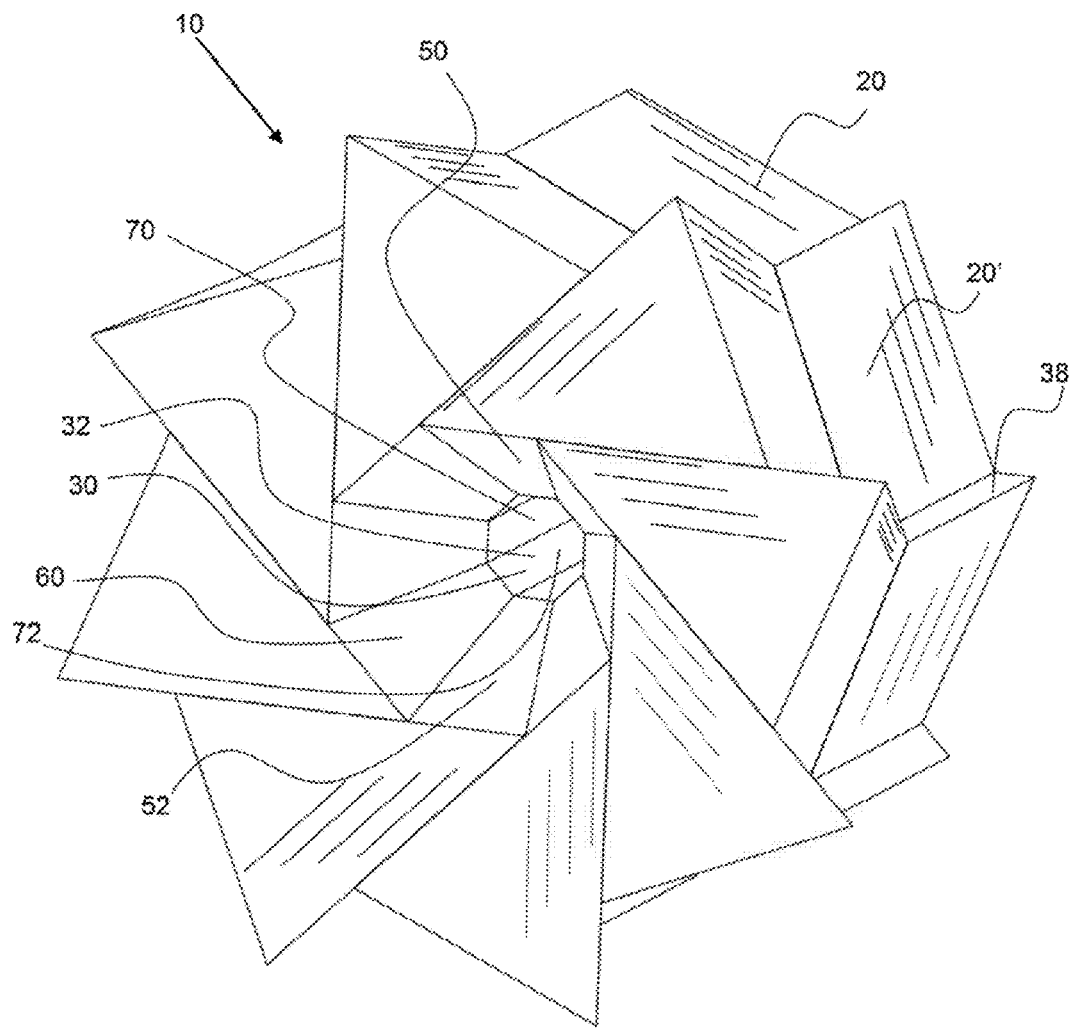
FIG. 8 shows a perspective view of an exemplary radial compression mechanism comprising a plurality of compression dies configured radially about a central cylindrical cavity and having an introduction funnel formed from an introduction portion of the compression dies.

As shown in FIG. 8, an exemplary radial compression mechanism 10 comprises a plurality of compression dies 20 configured radially about a central cylindrical cavity 70 and has an introduction funnel 60 formed from an introduction portion 50 of the compression dies. Each die comprises a compression portion 30 and an introduction portion 50. The compression portion 30 comprises a die working surface 32 that forms the cylindrical cavity 70. The introduction portion comprising an introduction surface 52 that forms the introduction funnel 60, having a funnel surface. The introduction funnel enables articles to be easily fed into the compression portion, or the cylindrical cavity for compression. The funnel surface and the cavity surface 72 may be substantially continuous, having less than about 2.5 um gap between adjacent compression dies.

Figure 9:
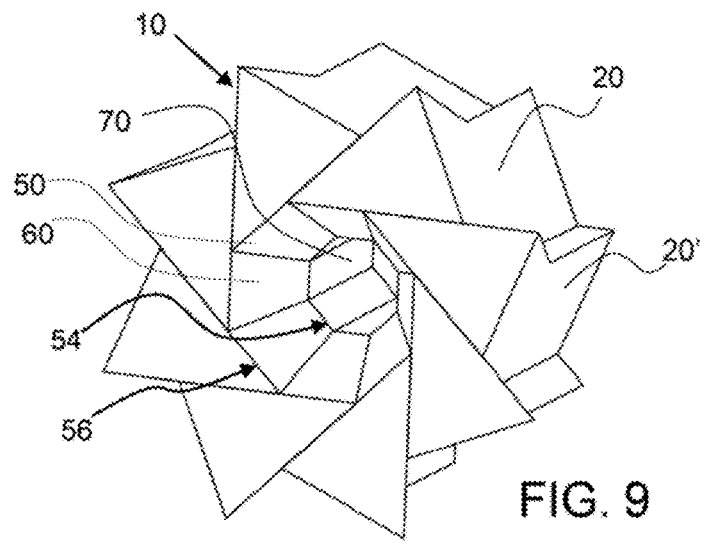
FIGS. 9 to 11 show perspective views of an exemplary radial compression mechanism in a range of positions, from an open position, FIG. 9, to a closed position, FIG. 11.
Figure 10:
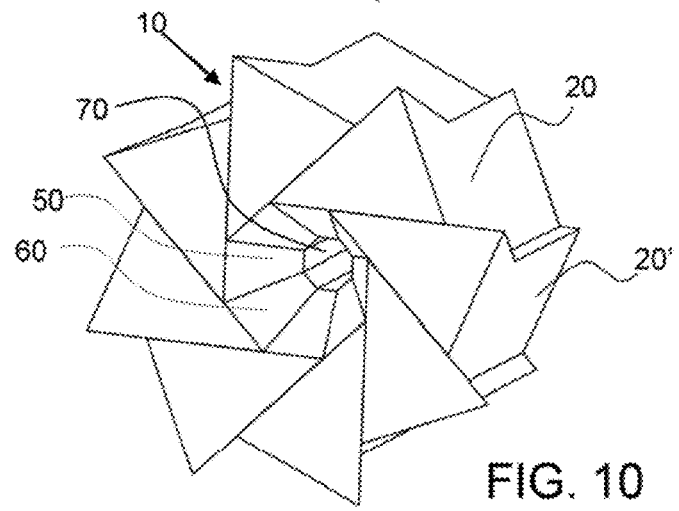
Figure 11:
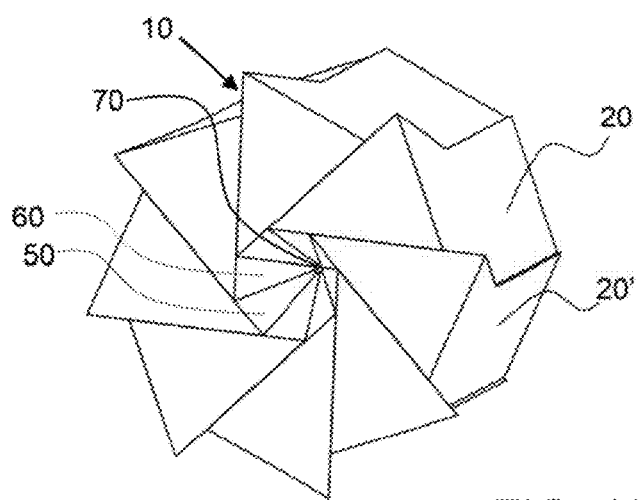

As shown in FIGS. 9 to 11, an exemplary radial compression mechanism 10 is in a range of positions, from an open position, FIG. 9, to a closed position, FIG. 11. FIG. 10 may represent the radial compression mechanism in a compressed diameter, or a desired diameter for an article. The introduction funnel 60 and the cylindrical cavity 70 change in diameter as the plurality of compression dies 20 move. The introduction portion 50 of each of the compression dies 20 has an attached end 54, and an extended end 56.

Figure 12:
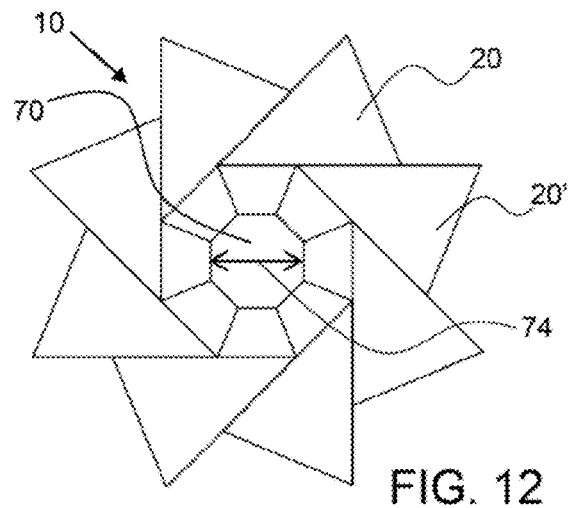
FIGS. 12 to 14 show front views of an exemplary radial compression mechanism in a range of positions, from an open position, FIG. 12, to a closed position, FIG. 14.
Figure 13:
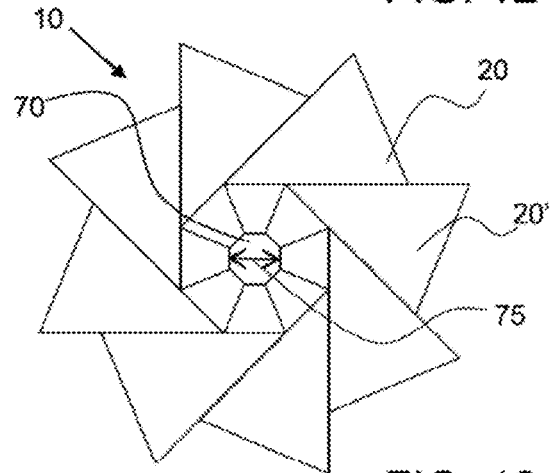
Figure 14:
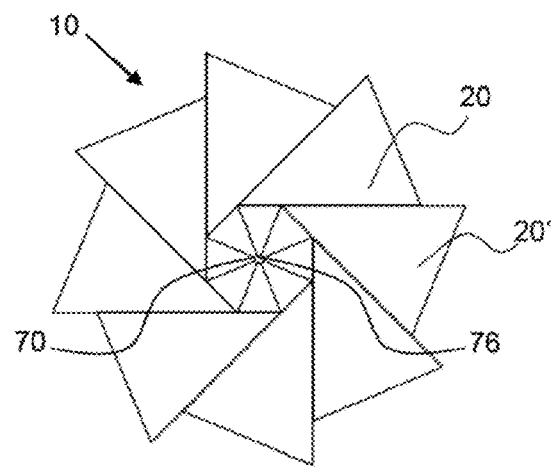

As shown in FIGS. 12 to 14, an exemplary radial compression mechanism 10 is in a range of positions, from an open position, FIG. 12, to a closed position, FIG. 14. The central cavity diameter changes from an open diameter 74, as shown in FIG. 12, to a closed diameter 76, as shown in FIG. 14. A desired compression diameter 75 of the central cavity is shown in FIG. 13. The closed diameter may be substantially zero wherein the working surfaces of the plurality of compression dies touch.

Figure 15:
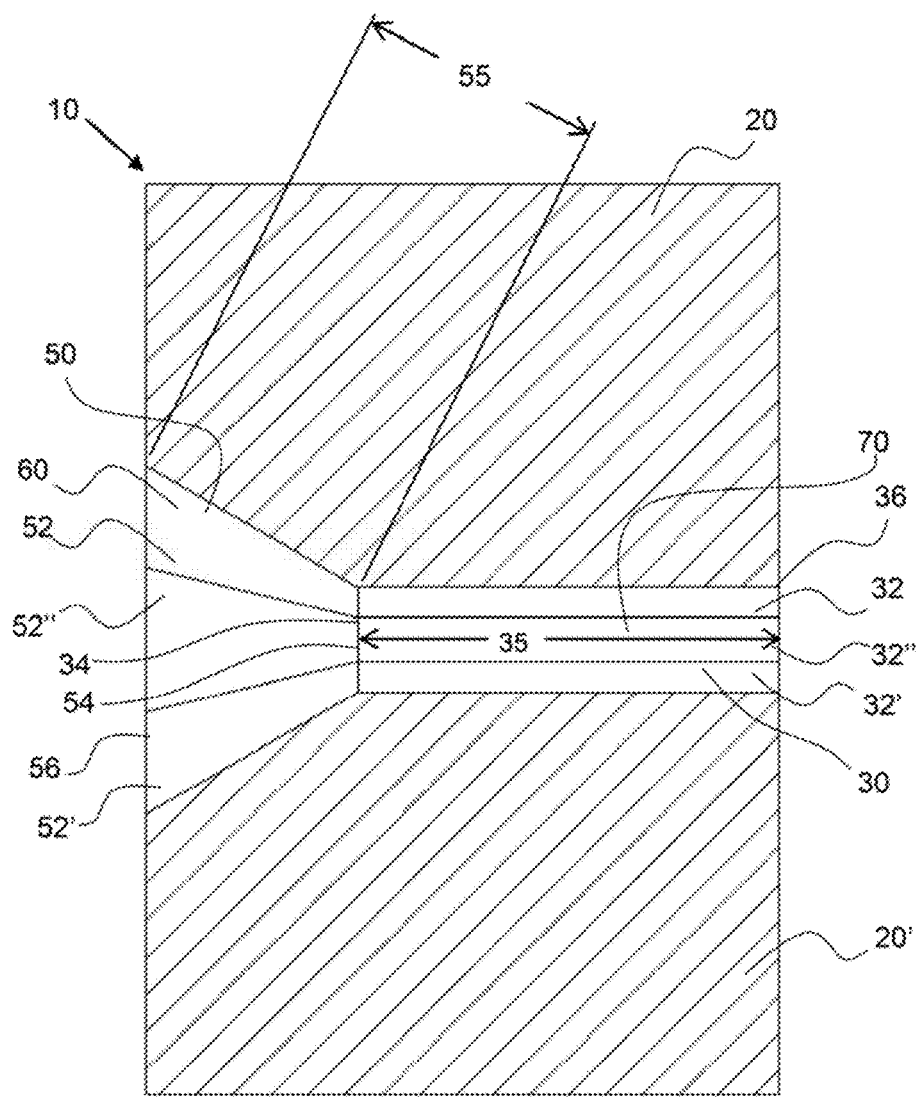
FIG. 15 shows a cross-sectional view of an exemplary radial compression mechanism comprising a plurality of compression dies that form an introduction funnel and a cylindrical cavity.

As shown in FIG. 15, an exemplary radial compression mechanism 10 comprises a plurality of compression dies 20 that form an introduction funnel 60 and a cylindrical cavity 70. The central cavity is formed by the plurality of working surfaces 32-32" of the compression portion 30 of the compression dies. The introduction funnel is formed by the introduction surfaces 52-52" of the introduction portion 50 of the compression dies. The cylindrical cavity 70 has a length 35 formed from the working surfaces 32, from an inlet end 34 to an exit end 36. The introduction funnel 60 extends from the extended end 56 to the attached end 54 of the introduction portion 50 of the compression dies 20. The length of the introduction surface 55 is shown.

Figure 16:
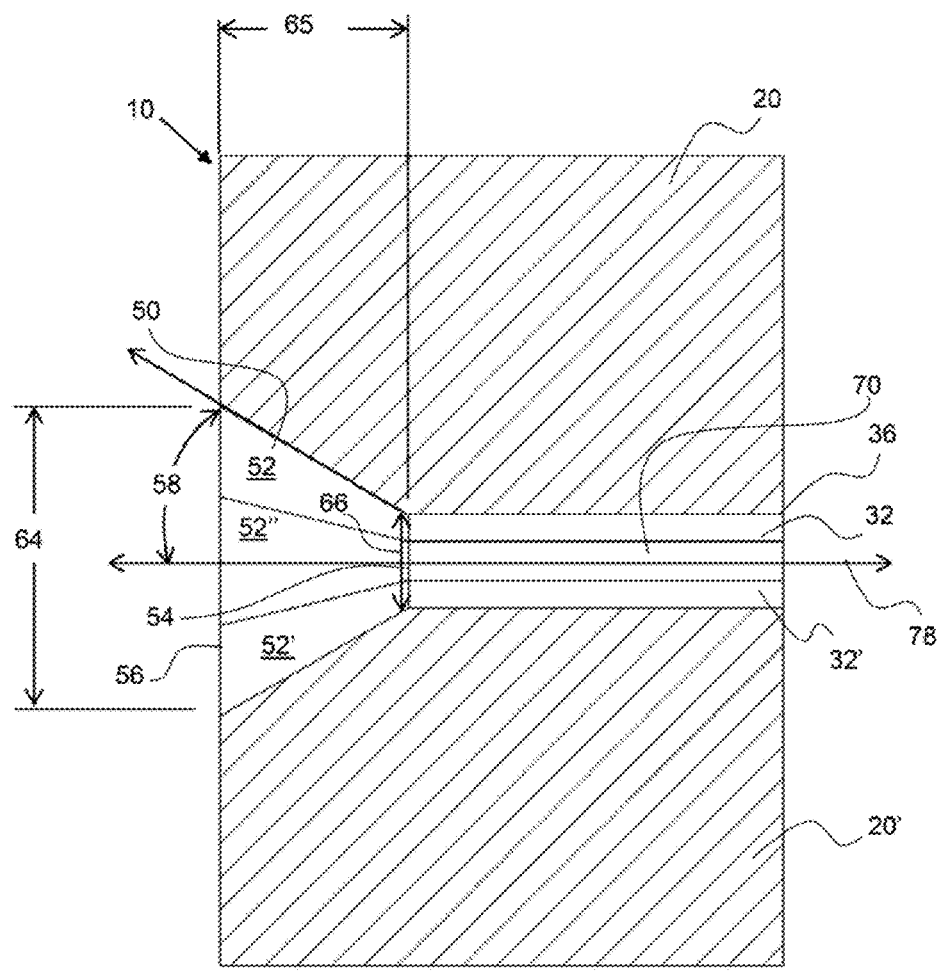
FIG. 16 shows a cross-sectional view of an exemplary radial compression mechanism comprising a plurality of compression dies that form an introduction funnel and a cylindrical cavity.

As shown in FIG. 16, an exemplary radial compression mechanism 10 comprises a plurality of compression dies 20 that form an introduction funnel 60 and a cylindrical cavity 70. The funnel extended end diameter 64 is larger than the funnel attached end diameter 66 and the introduction surfaces 52 of the compression dies 20 are configured at an introduction angle 58 to a central axis 78 that extends through the cylindrical cavity 70. The introduction funnel 60 has a length 65 from the extended end 56 to the attached end 54, or where the introduction surfaces 52 couple with the working surfaces 32 of the compression dies 20.

Figure 17:
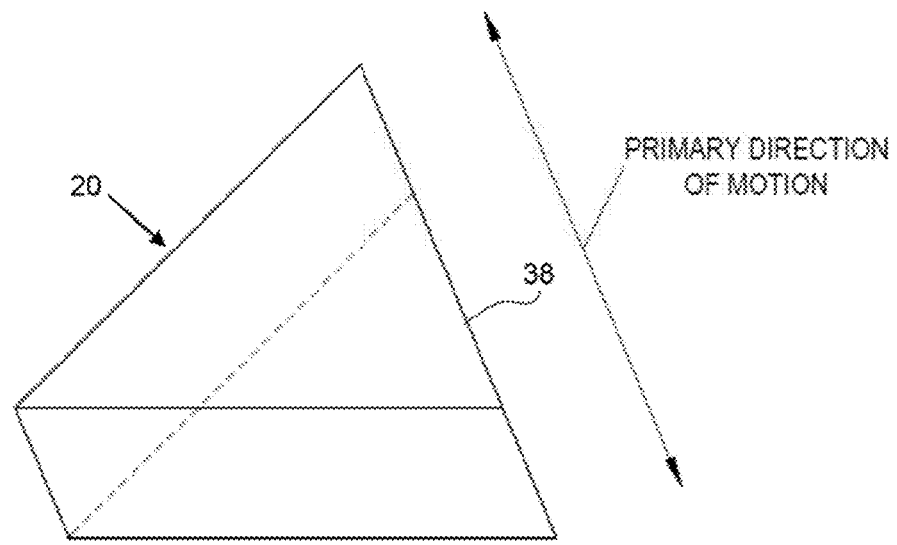
FIG. 17 shows a perspective view of a portion of an exemplary compression die having an interface surface.

As shown in FIG. 17, an exemplary compression die has an interface surface that is along the primary direction of motion.

Figure 18:
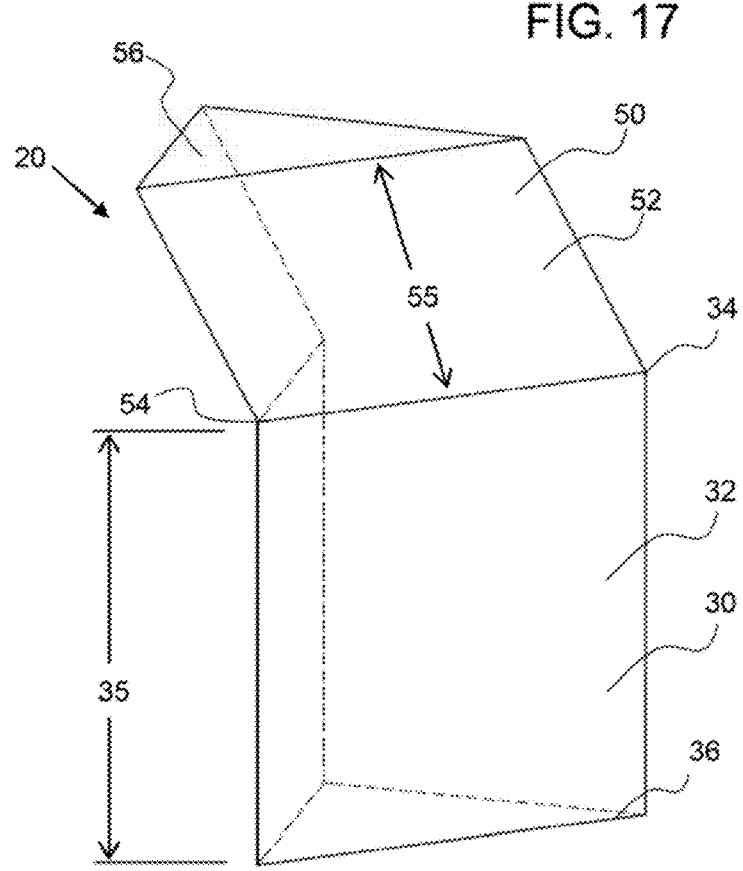
FIG. 18 shows a perspective view of an exemplary compression die having a compression portion and an introduction portion.

As shown in FIG. 18, an exemplary compression die 20 has a compression portion 03 and an introduction portion 50. The compression portion has a working surface 32 that is planar and has a length from an inlet end 34 to an exit end 36. The introduction portion has an introduction surface 52 that is planar and has a length 55 from the extended end 56 to the attached end 54.

Figure 19:
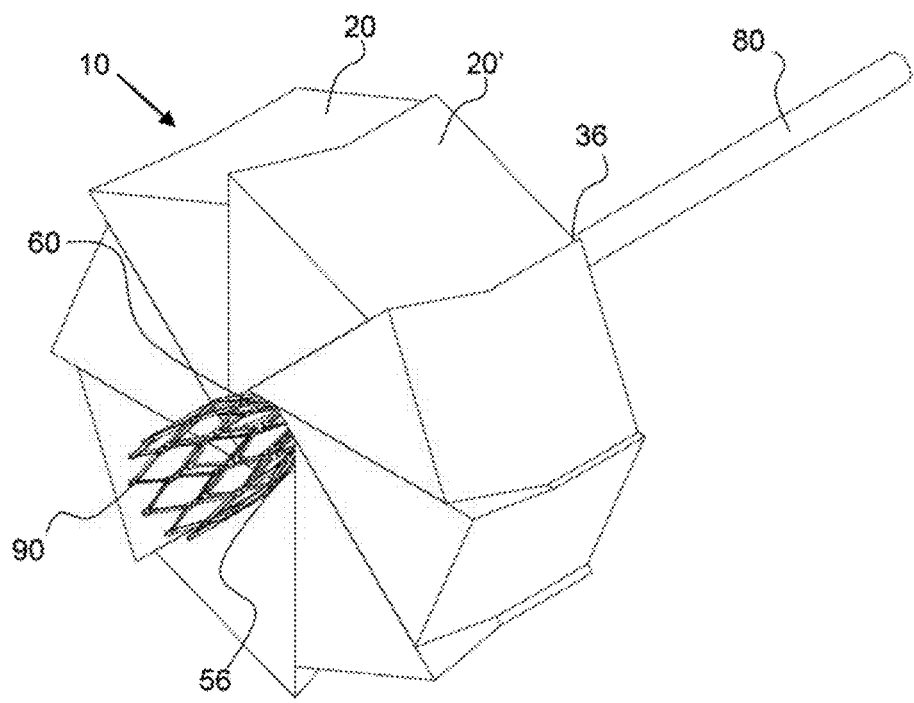
FIG. 19 shows a perspective view of an exemplary radial compression mechanism compressing a stent and loading the compressed stent into a delivery catheter.

As shown in FIG. 19, an exemplary radial compression mechanism 10 is compressing a stent 90 and loading the compressed stent into a delivery catheter 80. The stent has a free diameter, or diameter with no external forces applied, as shown extending out from the introduction funnel 60. The stent is extending through the introduction funnel and into the compression portion, wherein it is radially compresses from an inlet diameter to a compressed diameter.

Figure 20:
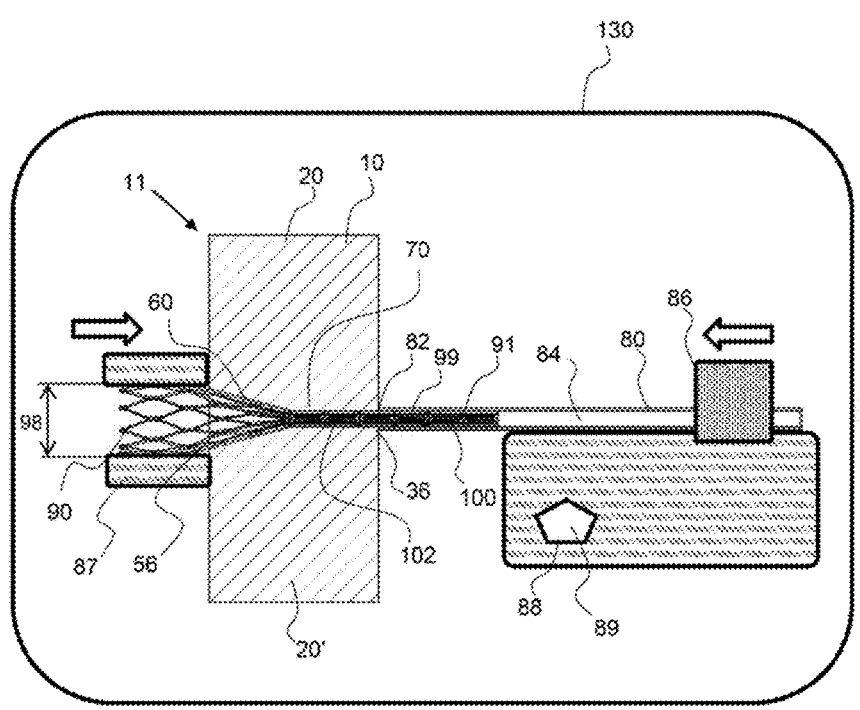
FIG. 20 show a side cross-sectional view of an exemplary radial compression mechanism compressing a stent and loading the compressed stent into a delivery catheter.

As shown in FIG. 20, an exemplary radial compression system 11 comprises a radial compression mechanism 10 that is compressing a stent 90 and loading the radially compressed stent 91 into a delivery catheter 80. The second article portion 102 of the compressed stent 91 is retained within the conduit 84 of the delivery catheter. The stent is partially radially compressed as it extends into the introduction funnel 60 from the extended end 56 to the cylindrical cavity 70. The compressed stent 91 exits the radial compression mechanism 10 at the exit end 36, where a first article portion 100, or a portion of the article, stent, previously compressed is pushed out of the exit end 36 of the cylindrical cavity 70. The first article portion 100 is slid into the insertion end 82 of the catheter 80. The diameter of the stent 98 before radial compression is much larger than the compressed diameter of the stent 99. A catheter drive mechanism 86 is configured to move the catheter over the compresses stent portions incrementally. A control 88, which may comprise a microprocessor 89, may be used to synch the catheter drive mechanism 86, with the radial compression mechanism 10 and/or an article drive mechanism 87, configured to feed an article into the radial compression mechanism. In an exemplary embodiment, the controller 88, runs a control program that synchronizes the article drive mechanism 87 as well as the catheter drive mechanism 86 with the opening and closing of the cylindrical cavity 70. An incremental compressing and insertion method may be operated at high frequencies, wherein a compressed portion of the article is loaded into the delivery catheter every second, or preferably five to ten time per second and even more preferably, 30 to 60 times per second. The entire incremental radial compression system 11 may be configured in a temperature control device 130, such as a heater, oven or refrigerator to maintain a desired temperature of the article, or stent. In may be preferred to keep a stent below a transition temperature, wherein the stent is engineered to expand to a preset dimension. This temperature may be near or about body temperature or about 37° C.

Figure 21:
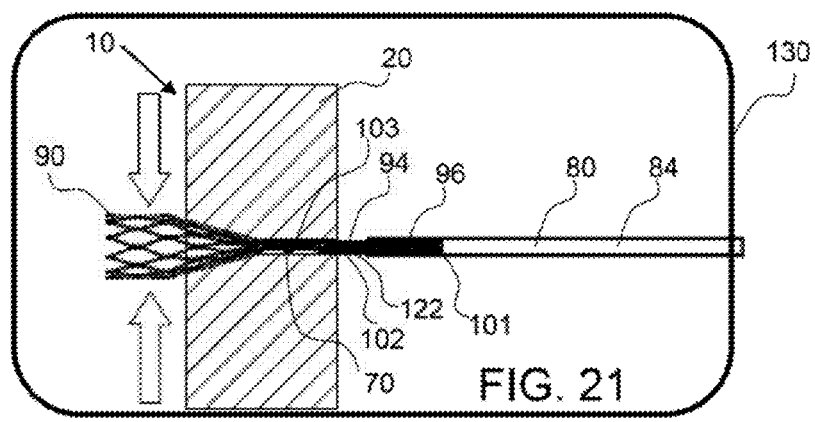
FIGS. 21 to 24 show a cross-sectional view an exemplary radial compression mechanism incrementally compressing a stent and loading it into a delivery catheter.
Figure 22:
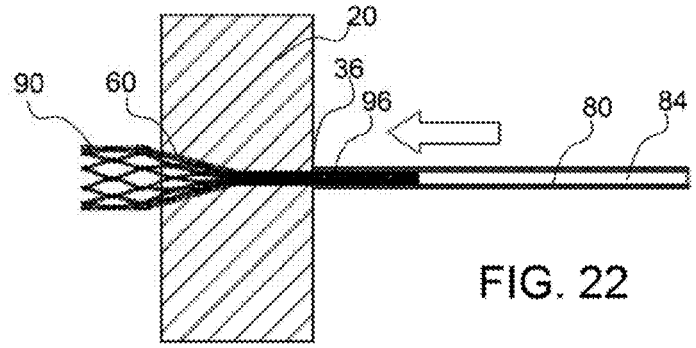
Figure 23:
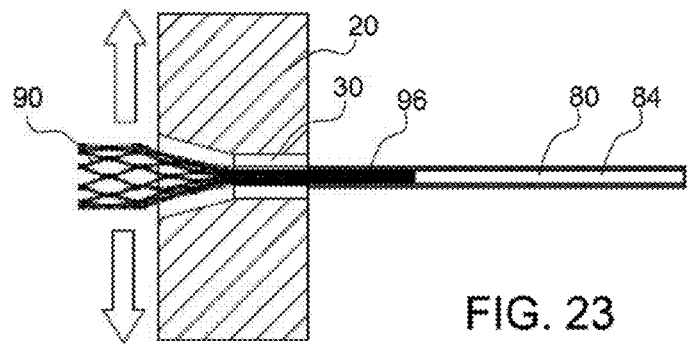
Figure 24:
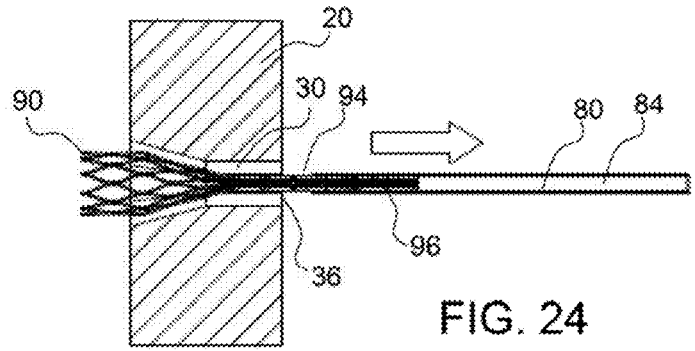

As shown in FIGS. 21 to 24, an exemplary radial compression mechanism 10 is incrementally compressing a stent 90 and loading it into a delivery catheter 80. In FIG. 21, a third article portion 103 of the stent is radially compressed and is retained in the cylindrical cavity 70. A second article portion 102, a portion of the stent previously compressed in the cylindrical cavity to form a compressed article portion 122, extends from the exit end 36 of the cylindrical cavity 70 and is ready to be inserted into the catheter. A first article portion 100, a portion of the stent compressed before the second article portion by the compression portion to also form a compressed article portion, is now an inserted portion 96, as it is inserted into the catheter 80. An extended compressed portion 94 of the stent is compressed and extends from the radial compression mechanism 10. While the radial compression mechanism is in a compressed position, with a portion of the stent being compressed in the cylindrical cavity, or compression portion 30, the catheter is push over the extended compressed portion 94 of the stent, as shown in FIG. 22. In FIG. 23, the radial compression mechanism is opened and in FIG. 24 a new increment of the stent is inserted into the compression portion, thereby pushing a new extended compressed portion 94 out of the exit end 36. The process can be repeated by compressing the stent, opening the radial compression mechanism 10 and indexing the stent out of the exit end 36 of the cylindrical portion 70, recompressing a new portion of the stent and while compressed pushing the catheter over the extended compressed portion. This method demonstrates how increments of the stent can be compressed and loaded into a delivery catheter. This process may be conducted at a temperature that is conducive to compressing the stent and maintaining the stent in a compressed state, such as below a transition temperature of a stent material, such as Nitinol. A temperature control device 130, as shown in FIG. 21 as an example, may be used to keep a stent below a transition temperature that may be about body temperature or about 37° C.

It will be apparent to those skilled in the art that various modifications, combinations and variations can be made in the present invention without departing from the spirit or scope of the invention. Specific embodiments, features and elements described herein may be modified, and/or combined in any suitable manner. Thus, it is intended that the present invention cover the modifications, combinations and variations of this invention provided they come within the scope of the appended claims and their equivalents.

What is claimed is:

1. A radial compression mechanism comprising:
   a) a base;
   b) a plurality of compression dies wherein each of said compression dies comprises:
      i) a compression portion comprising:
         1) a die working surface having a length from an inlet end and an exit end;
      ii) an introduction portion comprising:
         1) an introduction surface having a length from an attached end to an extended end;
      wherein the introduction portion is attached to the compression portion at the inlet end of the compression portion and wherein the introduction surface extends at an introduction angle that is an acute angle from the working surface;
      wherein the introduction surfaces of the plurality of compression dies form an introduction funnel having a substantially continuous funnel surface having no more than a 250 µm gap between adjacent introduction surfaces from said open and closed position;
      wherein said plurality of compression dies are arranged radially with respect to each other to form a generally centrally located cylindrical cavity defined by the working surfaces and having a length from said inlet end to said exit end;
      wherein the cylindrical cavity has a substantially continuous surface having no more than a 250 µm gap between adjacent die working surfaces from said open and closed position; and
      wherein the plurality of compression dies are coupled to said base and configured to move in unison from an open position, wherein the cylindrical cavity is in an open position having an open cavity diameter, to a closed position, wherein the cylindrical cavity is in a closed position having a closed cavity diameter;
      wherein said open cavity diameter is larger than said closed cavity diameter;
   c) a drive mechanism coupled with each of the plurality of compression dies to move each of the dies in unison from an open position to a closed position.

2. The radial compression mechanism of claim 1, comprising at least three compression dies.

3. The radial compression mechanism of claim 1, wherein the acute angle is at least 5 degrees.

4. The radial compression mechanism of claim 1, wherein acute angle is between 3 and 60 degrees.

5. The radial compression mechanism of claim 1, wherein a maximum open cavity diameter of the cylindrical cavity it at least two times greater in dimension than the length of the cylindrical cavity.

6. The radial compression mechanism of claim 1, wherein the closed cylindrical cavity diameter is no more than 100 µm.

7. The radial compression mechanism of claim 1, wherein the length of the introduction surface is at least as long as the length of the cylindrical cavity.

8. The radial compression mechanism of claim 1, wherein the introduction portion of at least a some of the plurality of compression dies are integrally attached to the compression portion, wherein the introduction portion and the compression portion are a one-piece unit formed from a single piece of material.

9. The radial compression mechanism of claim 1, further comprising:
   a) a delivery catheter;
   b) a catheter drive mechanism;
   c) a controller;
      wherein the drive mechanism pushes the delivery catheter over a radially compressed article after it is pushed out of the exit end of the cylindrical cavity; and
      wherein the controller controls the catheter drive mechanism with respect to the cylindrical cavity position, whereby the catheter is pushed over compressed article when the plurality of compression dies are in a compressed position.

10. The radial compression mechanism of claim 9, further comprising:
    a) an article drive mechanism;
       wherein the article drive mechanism pushes the article into the cylindrical cavity, and
       wherein the controller controls the article drive mechanism with respect to the cylindrical cavity, whereby the article is pushed into the cylindrical cavity when the plurality of compression dies are in an open position.

11. A method of compressing an article comprising the steps of:
    a) providing an incremental radial compression system comprising a radial compression mechanism comprising:
       i) a base;
       ii) a plurality of compression dies wherein each of said compression dies comprises:
          a compression portion comprising:
             a die working surface having a length from an inlet end and an exit end;
          an introduction portion comprising:
             an introduction surface having a length from an attached end to an extended end;
          wherein the introduction portion is attached to the compression portion at the inlet end of the compression portion and wherein the introduction surface extends at an introduction angle that is an acute angle from the working surface;
          wherein the introduction surfaces of the plurality of compression dies form an introduction funnel having a substantially continuous funnel surface having no more than a 250 µm gap between adjacent introduction surfaces from said open and closed position;
          wherein said plurality of compression dies are arranged radially with respect to each other to form a generally centrally located cylindrical cavity defined by the working surfaces and having a length from said inlet end to said exit end;
          wherein the cylindrical cavity has a substantially continuous surface having no more than a 250 µm gap between adjacent die working surfaces from said open and closed position; and
          wherein the plurality of compression dies are coupled to said base and configured to move in unison from an open position, wherein the cylindrical cavity is in an open position having an open cavity diameter, to a closed position, wherein the cylindrical cavity is in a closed position having a closed cavity diameter;
       wherein said open cavity diameter is larger than said closed cavity diameter;

a drive mechanism coupled with each of the plurality of compression dies to move each of the dies in unison from an open position to a closed position;

b) providing an article having a length and a free diameter;

c) positioning the plurality of compression dies in an open position;

d) inserting a first article portion through the introduction funnel and into the cylindrical central cavity;

e) closing the radial compression mechanism, wherein the plurality of compression dies are forced to a compression position to produce a first compressed article portion from said first article portion;

wherein the first compressed article portion is compressed to a compressed diameter that is less than the free diameter;

f) opening the radial compression mechanism and incrementing a second article portion through the introduction funnel and into the cylindrical cavity, whereby the first compressed article portion is forced out of the exit end of the cylindrical central cavity to form an extended compressed portion;

g) closing the radial compression mechanism, wherein the plurality of compression dies are forced to said compressed position to produce a second compressed article portion from said second article portion;

wherein the second article portion is compressed to a compressed diameter that is less than the free diameter;

removing the article from the radial compression mechanism to produce a radially compressed article.

12. The method of compressing an article of claim 11, wherein the steps of opening the radial compression mechanism and incrementing the second article portion into the cylindrical cavity for compression and compressing said second article portion and opening the radial compression mechanism is performed at a rate of 0.2 seconds or less.

13. The method of compressing an article of claim 11, wherein the steps of opening the radial compression mechanism and incrementing the second article portion into the cylindrical cavity for compression and compressing said second article portion and opening the radial compression mechanism is performed at a rate of at least 30 hz.

14. The method of compressing an article of claim 11, further comprising the step of:
a) cooling the delivery catheter to a temperature less than a transition temperature of the article.

15. The method of compressing an article of claim 11, further comprising the steps of:
a) providing a delivery catheter,
b) positioning the delivery catheter over the extended compressed portion of the article as it is indexed out from the exit end of the cylindrical cavity; and
c) incrementally inserting subsequent extended compressed portions into the catheter as it compressed by the radial compression mechanism.

16. The method of compressing an article of claim 15, wherein the article is a stent.

17. The method of compressing an article of claim 15, wherein the article is a self-expanding stent.

18. The method of compressing an article of claim 15, further comprising the step of:
a) cooling the delivery catheter to a temperature less than a transition temperature of the article and keeping the extended compressed portion of the article below said transition temperature until it is inserted into the catheter.

19. The method of compressing an article of claim 15, further comprising the steps of:
a) providing a catheter drive mechanism;
b) a controller;
wherein the drive mechanism pushes the delivery catheter over the radially compressed article; and
wherein the controller controls the catheter drive mechanism with respect to the radial compression mechanism, whereby the catheter is pushed over extended compressed portion of the article when the plurality of compression dies are in a compressed position.

20. The method of compressing an article of claim 19, further comprising the steps of:
a) providing an article drive mechanism;
wherein the article drive mechanism pushes the article into the radial compression mechanism, and
wherein the controller controls the article drive mechanism with respect to the radial compression mechanism, whereby the article is pushed into the cylindrical cavity when the plurality of compression dies are in an open position.

21. The method of compressing an article of claim 20, wherein the article is a stent.

22. The method of compressing an article of claim 20, wherein the article is a self-expanding stent.

* * * * *